(12) United States Patent
Daubersies et al.

(10) Patent No.: US 10,576,025 B2
(45) Date of Patent: *Mar. 3, 2020

(54) COMPOSITION COMPRISING POLYMER PARTICLES, A HYDROCARBON-BASED OIL AND A HYDROCARBON-BASED BLOCK COPOLYMER, AND PROCESS USING THE SAME

(71) Applicant: L'OREAL, Paris (FR)

(72) Inventors: Laure Daubersies, Paris (FR); Christel Lison, Sain-Ouen (FR); Stephane Douezan, Le Kremlin Bicetre (FR); Hy Si Bui, Piscataway, NJ (US); Rita El-Khouri, Morristown, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/535,963

(22) PCT Filed: Dec. 18, 2015

(86) PCT No.: PCT/US2015/066684
§ 371 (c)(1),
(2) Date: Jun. 14, 2017

(87) PCT Pub. No.: WO2016/100821
PCT Pub. Date: Jun. 23, 2016

(65) Prior Publication Data
US 2017/0360657 A1  Dec. 21, 2017

Related U.S. Application Data

(60) Provisional application No. 62/093,946, filed on Dec. 18, 2014.

(51) Int. Cl.
| | |
|---|---|
| *A61Q 1/04* | (2006.01) |
| *A61K 8/02* | (2006.01) |
| *A61K 8/81* | (2006.01) |
| *A61K 8/90* | (2006.01) |
| *A61Q 1/06* | (2006.01) |
| *A61Q 1/10* | (2006.01) |
| *A61K 8/31* | (2006.01) |
| *C08L 33/10* | (2006.01) |
| *C08L 33/08* | (2006.01) |
| *C09D 133/08* | (2006.01) |

(52) U.S. Cl.
CPC ............. *A61K 8/0241* (2013.01); *A61K 8/31* (2013.01); *A61K 8/8152* (2013.01); *A61K 8/8164* (2013.01); *A61K 8/90* (2013.01); *A61Q 1/04* (2013.01); *A61Q 1/06* (2013.01); *A61Q 1/10* (2013.01); *C09D 133/08* (2013.01); *A61K 2800/52* (2013.01); *A61K 2800/594* (2013.01); *A61K 2800/5922* (2013.01); *A61K 2800/614* (2013.01); *A61K 2800/654* (2013.01)

(58) Field of Classification Search
None
See application file for complete search history.

(56) References Cited

U.S. PATENT DOCUMENTS

| | | | |
|---|---|---|---|
| 5,616,598 A | 4/1997 | Lion et al. | |
| 5,851,517 A | 12/1998 | Mougin et al. | |
| 5,945,095 A | 8/1999 | Mougin et al. | |
| 9,895,561 B2 | 2/2018 | Ilekti et al. | |
| 2004/0120920 A1 | 6/2004 | Lion et al. | |
| 2004/0137028 A1 | 7/2004 | de la Poterie | |
| 2004/0234612 A1* | 11/2004 | Blin ...................... | A61K 8/375 424/489 |
| 2006/0193803 A1* | 8/2006 | Farcet .................... | A61K 8/31 424/70.1 |

(Continued)

FOREIGN PATENT DOCUMENTS

| | | |
|---|---|---|
| EP | 0 749 746 | 12/1996 |
| EP | 0 749 747 | 12/1996 |
| FR | 2 785 530 | 5/2000 |
| FR | 2 937 645 | 4/2010 |
| FR | 2 972 630 | 9/2012 |
| FR | 2 972 631 | 9/2012 |

(Continued)

OTHER PUBLICATIONS

International Search Report and Written Opinion dated Apr. 14, 2016 in PCT/US2015/066684, filed on Dec. 18, 2015.

(Continued)

*Primary Examiner* — Monica A Shin
(74) *Attorney, Agent, or Firm* — Oblon, McClelland, Maier & Neustadt, L.L.P.

(57) ABSTRACT

The present invention relates to a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one amorphous hydrocarbon-based block copolymer obtained by polymerization of at least one monomer of unsaturated hydrocarbon type comprising 2 to 5 carbon atoms and containing one or two ethylenic unsaturations. The invention also relates to a process for making up and/or caring for keratin materials, in which said composition is applied.

18 Claims, No Drawings

(56) References Cited

U.S. PATENT DOCUMENTS

| | | |
|---|---|---|
| 2010/0047353 A1 | 2/2010 | Batra et al. |
| 2011/0243864 A1 | 10/2011 | Farcet et al. |
| 2011/0305650 A1 | 12/2011 | Herzog et al. |
| 2012/0294817 A1* | 11/2012 | Kawaratani ............... A61Q 1/06 424/64 |

FOREIGN PATENT DOCUMENTS

| | | |
|---|---|---|
| JP | 2004-256538 A | 9/2004 |
| JP | 2006-510734 A | 3/2006 |
| JP | 2006-213717 A | 8/2006 |
| KR | 10-2004-0076808 A | 9/2004 |
| KR | 10-2014-0072216 A | 6/2014 |
| WO | WO 2013/190702 A1 | 12/2013 |

OTHER PUBLICATIONS

Korean Office Action dated Jun. 5, 2108 in Korean Patent Application No. 10-2017-7016642 (with English translation), citing documents AO, AP and AQ therein, 18 pages.
U.S. Appl. No. 14/575,259, filed Dec. 18, 2014, 2016/0175204, Rita Jaky El-Khouri.
U.S. Appl. No. 14/575,419, filed Dec. 18, 2014, 2016/0175230, Susan Halpern-Chirch.
U.S. Appl. No. 14/575,866, filed Dec. 18, 2014, US2016/0175232, Rita Jaky El-Khouri.
U.S. Appl. No. 14/974,531, filed Dec. 18, 2015, 2016/0184211, Roshanak Debeaud.
U.S. Appl. No. 14/974,706, filed Dec. 18, 2015, 2016/0175205, Roshanak Debeaud.
U.S. Appl. No. 15/105,293, filed Jun. 16, 2016, 2016/0317423, Julien Portal.
U.S. Appl. No. 15/533,444, filed Jun. 6, 2017, Hong Li.
U.S. Appl. No. 15/534,216, filed Jun. 8, 2017, Roshanak Debeaud.
U.S. Appl. No. 15/537,082, filed Jun. 16, 2017, Laure Daubersies.
U.S. Appl. No. 15/537,422, Philippe Ilekti.
U.S. Appl. No. 15/537,423, Philippe Ilekti.
Office Action dated Jul. 24, 2018 in Japanese Patent Application No. 2017-532713, citing documents AO-AQ therein, 4 pages.
Korean Office Action dated Jan. 25, 2019 in Korean Application No. 10-2017-7016642 (with English Translation).
Korean Office Action dated May 13, 2019 in Korean Application No. 10-2017-7016642 (with English Translation).
Korean Office Action dated Oct. 16, 2019 in Korean Application No. 10-2017-7016642, filed Jun. 16, 2017 (with English Translation).

* cited by examiner

COMPOSITION COMPRISING POLYMER PARTICLES, A HYDROCARBON-BASED OIL AND A HYDROCARBON-BASED BLOCK COPOLYMER, AND PROCESS USING THE SAME

The present invention relates to compositions for making up and/or caring for human keratin materials, in particular the lips and keratin fibres in particular especially the eyelashes, comprising polymer particles, at least one hydrocarbon-based oil and at least one particular hydrocarbon-based block copolymer.

These compositions are well known and, although they have specific properties as a function of their use, there has been a very clear tendency in recent years to develop compositions whose persistence is improved. This avoids, on the one hand, the need to reapply the composition too often and, on the other hand, reduces transfer onto supports with which the made-up areas might come into contact (clothing, cups, etc.) or else their removal via the action of external agents (sebum, food, rain, etc.).

That is why the compositions for which this property is sought generally comprise at least one film-forming agent. This agent is quite often a polymer, which is in a solubilized form or dispersed in one of the phases of the composition. It allows the composition, once applied, to form after drying a film that is more cohesive and persistent on the support.

One of the problems encountered with such film-forming agents lies in the fact that the compositions containing them give a deposit that, once dry, notably loses its shine. But this can be perceived as a disadvantage in the case of certain applications.

The use of very glossy film-forming agents, such as those used in nail varnish compositions, is clearly unsuitable for compositions for making up the lips or the eyelashes, for example. The reason for this is that the film obtained would be considered too rigid for this type of support, and thus uncomfortable. In addition, the deposit would run the risk of being brittle, which would result in crumbling of the composition once dried.

As an alternative to this problem, it has been proposed to use compositions in two steps, the first consisting in applying the composition containing the film-forming agent which ensures good persistence, and the second providing the gloss. These processes represent an improvement in terms of the gloss of the deposit, but they are more complicated than standard one-step processes. Also, they cannot be transposed to all makeup compositions.

Another route envisaged is to add to the composition at least one non-volatile glossy oil. In this case also, this process cannot be used for all types of makeup composition, in particular those for which the deposit is expected to dry relatively quickly, to limit the tacky sensation during this period, and also the risks of the composition running outside the made-up area.

Compositions are thus sought which comprise at least one film-forming agent, which do not have the abovementioned disadvantages.

One subject of the invention is thus a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one amorphous hydrocarbon-based block copolymer obtained by polymerization of at least one monomer of unsaturated hydrocarbon type comprising 2 to 5 carbon atoms and containing one or two ethylenic unsaturations.

A subject of the invention is also a process for making up and/or caring for keratin materials, in particular the lips and keratin fibres especially such as the eyelashes and the eyebrows, which consists in applying said composition.

It has in fact been observed that the composition according to the invention results in non-tacky, resistant deposits that remain shiny after drying. In addition, the composition according to the invention is easy to apply, comfortable and can be used in various makeup applications (lips, keratin fibres such as the eyelashes, especially the eyebrows).

However, other advantages will emerge more clearly on reading the description and the examples that follow.

It should be noted that, in the remainder of the description, unless otherwise indicated, the limits indicated for a range are included in that range.

The expressions "at least one" and "several" are used without distinction.

Hydrocarbon-Based Oil

The composition according to the invention comprises a hydrocarbon-based oil.

This oil may be volatile (vapour pressure greater than or equal to 0.13 Pa measured at 25° C.) or non-volatile (vapour pressure less than 0.13 Pa measured at 25° C.).

Preferably, the hydrocarbon-based oil is volatile.

The hydrocarbon-based oil is an oil (non-aqueous compound) that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:
hydrocarbon-based oils containing from 8 to 16 carbon atoms, and especially:
  branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl,
  linear alkanes, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, the mixtures of n-undecane ($C_{11}$) and of n-tridecane ($C_{13}$) obtained in Examples 1 and 2 of patent application WO 2008/155 059 from the company Cognis, and mixtures thereof,
  short-chain esters (containing from 3 to 8 carbon atoms in total) such as ethyl acetate, methyl acetate, propyl acetate or n-butyl acetate,
  hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleamrr, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, a mixture thereof.

More particularly, the content of hydrocarbon-based oil(s) ranges from 20% to 75% by weight, more particularly from 30% to 75% by weight and preferably from 40% to 60% by weight, relative to the weight of the composition.

This hydrocarbon-based oil may be provided totally or partly with the surface-stabilized polymer particles, in particular when these particles are introduced into the composition in the form of a pre-prepared dispersion of stabilized polymer particles. In this case, the hydrocarbon-based oil present in the composition represents at least the non-aqueous medium of the dispersion of polymer particles.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms and better still from 12 to 16 carbon atoms, in particular the apolar oils described previously.

Preferentially, the hydrocarbon-based oil is isododecane. More particularly, the isododecane content ranges from 20% to 75% by weight, more particularly from 30% to 75% by weight and preferably from 40% to 60% by weight, relative to the weight of the composition.

Preferably, the hydrocarbon-based oil(s), in particular isododecane, constitute the only oil(s) of the composition, or are present in a predominant weight content relative to the additional oil(s) that may be present in the composition.

In accordance with a particular embodiment of the invention, if the composition contains one or more non-volatile oils, their content advantageously does not exceed 20% by weight, more particularly does not exceed 10% by weight, preferably does not exceed 5% by weight relative to the weight of the composition, and better still does not exceed 2% by weight relative to the weight of the composition, or even is free of non-volatile oil(s).

Polymer Particles

The composition according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily (non-aqueous) medium, advantageously containing at least one hydrocarbon-based oil, as defined previously.

The polymer of the particles is a $C_1$-$C_4$ alkyl (meth)acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of $C_1$-$C_4$ alkyl (meth)acrylate and of 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth) acrylate and of (meth)acrylic acid or maleic anhydride.

The polymer of the particles may be chosen from:

methyl acrylate homopolymers ethyl acrylate homopolymers methyl acrylate/ethyl acrylate copolymers methyl acrylate/ethyl acrylate/acrylic acid copolymers methyl acrylate/ethyl acrylate/maleic anhydride copolymers methyl acrylate/acrylic acid copolymers ethyl acrylate/acrylic acid copolymers methyl acrylate/maleic anhydride copolymers ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 50 0000.

In the case of a particle dispersion, the polymer of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Advantageously, the stabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

Preferably, the stabilizer is soluble in the hydrocarbon-based oil(s), in particular soluble in isododecane.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface, in particular in order to keep these particles in dispersion in the non-aqueous medium of the dispersion.

According to a theory which should not limit the scope of the present invention, the inventors put forward the hypothesis that the surface stabilization of the $C_1$-$C_4$ alkyl (meth)acrylate polymer particles results from a phenomenon of surface adsorption of the stabilizer onto the $C_1$-$C_4$ alkyl (meth)acrylate polymer particles.

Advantageously, the combination of the stabilizer+polymer of the particles present in particular in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer+polymer of the particles.

Preferentially, the combination of the stabilizer+polymer of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer+polymer of the particles.

When the polymer particles are provided in the composition in the form of a pre-prepared dispersion, the oily medium of this polymer dispersion comprises a hydrocarbon-based oil. Reference may be made to that which has been indicated previously concerning this oil as regards its nature.

Advantageously, the hydrocarbon-based oil is apolar and preferably chosen from hydrocarbon-based oils containing from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of polymer particles that is suitable for use in the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a free-radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the free-radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of 5-20% by weight. The total amount of monomers may be present in the solvent before the start of the reaction, or part of the monomers may be added gradually as the polymerization reaction proceeds.

The free-radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

Moreover, the composition according to the invention advantageously comprises a content of surface-stabilized polymer particles described above of between 5% and 55% by weight, preferably between 5% and 50% by weight, more particularly from 8% to 45% by weight, preferably from 10% to 40% by weight, and even more preferentially from 10% to 25% by weight relative to the weight of the composition (content expressed as active material).

Block Hydrocarbon-Based Copolymer

As indicated previously, the composition according to the invention comprises at least one hydrocarbon-based copolymer bearing amorphous blocks, obtained by polymerization of at least one monomer of unsaturated hydrocarbon type comprising 2 to 5 carbon atoms and containing one or two ethylenic unsaturations.

These block hydrocarbon-based copolymers are preferably soluble or dispersible in the oily phase.

They may especially be of diblock, triblock, multiblock, radial or starburst type, or mixtures thereof.

Such block hydrocarbon-based copolymers are described, for example, in patent application US 2002/005 562 and in U.S. Pat. No. 5,221,534.

The copolymer may contain at least one block whose glass transition temperature is preferably less than 20° C., preferably less than or equal to 0° C., preferably less than or equal to −20° C. and more preferably less than or equal to −40° C. The glass transition temperature of said block may be between −150° C. and 20° C., especially between −100° C. and 0° C.

The term "amorphous polymer" means a polymer which has no crystalline form.

The monomer of unsaturated hydrocarbon type comprising 2 to 5 carbon atoms and having one or two ethylenic unsaturations may especially be an elastomeric ethylenically unsaturated monomer.

As examples of monomers of unsaturated hydrocarbon type comprising 2 to 5 unsaturated carbon atoms, mention may be made of ethylene, propylene, butadiene, isoprene or pentadiene.

Advantageously, the block hydrocarbon-based copolymer is an amorphous block copolymer of styrene and of hydrocarbon monomer(s) comprising 2 to 5 carbon atoms and comprising one or two ethylenic unsaturations.

Block copolymers comprising at least one styrene block and at least one block comprising units chosen from butadiene, ethylene, propylene, butylene and isoprene or a mixture thereof are especially preferred.

According to a preferred embodiment, the block hydrocarbon-based copolymer is hydrogenated to reduce the residual ethylenic unsaturations after polymerization of the monomers.

In particular, the hydrocarbon-based block copolymer is an optionally hydrogenated copolymer bearing styrene blocks and ethylene/$C_3$-$C_4$ alkylene blocks or isoprene blocks.

According to a preferred embodiment, the composition according to the invention comprises at least one diblock copolymer, which is preferably hydrogenated, preferably chosen from styrene-ethylene/propylene copolymers, styrene-ethylene/butadiene copolymers, styrene-ethylene/butylene copolymers and styrene-isoprene copolymers. The diblock polymers are especially sold under the name Kraton® G1701E by the company Kraton Polymers.

According to another preferred embodiment, the composition according to the invention comprises at least one triblock copolymer, which is preferably hydrogenated, preferably chosen from styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® D1101, Kraton® D1102 and Kraton® D1160 by the company Kraton Polymers.

According to one embodiment of the present invention, the hydrocarbon-based block copolymer is a styrene-ethylene/butylene-styrene triblock copolymer.

According to a preferred embodiment of the invention, use may be made especially of a mixture of a styrene-butylene/ethylene-styrene triblock copolymer and of a styrene-ethylene/butylene diblock copolymer, especially those sold under the name Kraton® G1657M by the company Kraton Polymers.

According to another preferred embodiment, the composition according to the invention comprises a mixture of hydrogenated styrene-butylene/ethylene-styrene triblock copolymer and of hydrogenated ethylene-propylene-styrene starburst polymer, such a mixture possibly being especially in isododecane or in another oil.

Such mixtures are sold, for example, by the company Penreco under the trade names Versagel® M5960 and Versagel® M5670.

Advantageously, a diblock copolymer such as those described previously is used as block hydrocarbon-based copolymer, in particular a styrene-ethylene/propylene diblock copolymer, or a mixture of diblock and triblock, as described previously, such as mixture of a styrene-butylene/ethylene-styrene triblock copolymer and of a styrene-ethylene/butylene diblock copolymer.

The block hydrocarbon-based copolymer(s) may be present in a content ranging from 2.5% to 15% by weight, relative to the total weight of the composition, preferably ranging from 2.5% to 8% by weight, relative to the total weight of the composition.

Additional Silicone Oils

The composition according to the invention may also comprise at least one additional volatile (saturating vapour pressure greater than or equal to 0.13 Pa at 25° C.) or non-volatile (saturating vapour pressure less than 0.13 Pa), and preferably volatile, silicone oil.

The term "silicone oil" means an oil containing at least one silicon atom, and especially containing Si—O groups.

Among the additional volatile silicone oils that are suitable for use, examples that may be mentioned include volatile linear or cyclic silicone oils, especially those with a viscosity≤8 centistokes ($8 \times 10^6$ m$^2$/s) and especially containing from 2 to 7 silicon atoms, these silicones optionally comprising alkyl or alkoxy groups containing from 1 to 10 carbon atoms.

As volatile silicone oils that may be used in the invention, mention may be made especially of octamethylcyclotetrasiloxane, cyclopentadimethylsiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of non-phenyl non-volatile silicone oils, for instance polydimethylsiloxanes (PDMS), PDMSs comprising aliphatic groups, in particular alkyl or alkoxy, which are pendent and/or at the end of the silicone chain; these groups each comprising from 2 to 24 carbon atoms. An example that may be mentioned is cetyl dimethicone sold under the commercial reference Abil Wax 9801 from Evonik Goldschmidt.

Non-volatile phenyl silicone oils optionally comprising one or more dimethicone fragments (—($CH_3$)$_2$—SiO—; this fragment is not at the extremity(ies) of the polymer) are also suitable, for instance phenyl trimethicones, phenyl dimethicones, phenyltrimethylsiloxydiphenylsiloxanes, diphenyl dimethicones and trimethylpentaphenyltrisiloxane, and mixtures thereof.

If the composition comprises any, the content of additional, preferably volatile, oil(s) varies between 1% and 15% by weight relative to the weight of the composition.

Preferably, the composition does not comprise more than 10% by weight, even more particularly not more than 5% by weight, of additional non-volatile oil, relative to the weight of the composition, and preferably does not contain any.

Waxes

The composition according to the invention may optionally comprise at least one wax.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C.

Hydrocarbon-based waxes, for instance beeswax, lanolin wax or Chinese insect wax; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may in particular be mentioned are hydrogenated jojoba oil, isomerized jojoba oil such as the trans-isomerized partially hydrogenated jojoba oil manufactured or sold by the company Desert Whale under the commercial reference Iso-Jojoba-50), hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, polypropylsilsesquioxane waxes (as described in patent WO 2005/100444), in particular with the C30-C45 alkyldimethylsilyl polypropylsilsesquioxane compound commercially available from Dow Corning under the brand name SW-8005 C30 Resin Wax.

The wax obtained by hydrogenation of olive oil esterified with the stearyl alcohol, sold under the name Phytowax Olive 18 L 57 or else the waxes obtained by hydrogenation of castor oil esterified with cetyl alcohol, sold under the names Phytowax Castor 16L64 and 22L73 by the company Sophim, may also be used. Such waxes are described in patent application FR-A-2 792 190.

If the composition comprises any, the content of wax may represent from 0.1% to 30% by weight and advantageously from 0.3% to 20% by weight relative to the weight of the composition.

In accordance with a particular embodiment of the invention, the content of wax does not exceed 10% by weight relative to the weight of the composition, and even more particularly does not exceed 5% by weight, relative to the weight of the composition. According to certain embodiments of the invention, the composition is free of wax.

Dyestuffs

The compositions in accordance with the invention may comprise at least one dyestuff.

This (or these) dyestuff(s) are preferably chosen from pulverulent substances, liposoluble dyes and water-soluble dyes, and mixtures thereof.

Preferably, the compositions according to the invention comprise at least one pulverulent dyestuff. The pulverulent dyestuffs may be chosen from pigments and nacres, and preferably from pigments.

The pigments may be white or coloured, mineral and/or organic, and coated or uncoated. Among the mineral pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions, especially of mascara type, are chosen from metal oxides.

More preferably, the pigments contained in the compositions according to the invention are chosen from iron oxides, such as especially those sold under the name Sunpuro Black Iron Oxide C33-7001® by the company Sun.

These dyestuffs may be present in a content ranging from 0.2% to 40% by weight and more particularly from 0.5% to 22% by weight, relative to the total weight of the composition. According to a more particular variant of the invention, the content of dyestuffs represents from 0.8% to 15% by weight relative to the total weight of the composition.

Fibres

The composition according to the invention may also comprise at least one fibre.

The term "fibre" should be understood as meaning an object of length L and of diameter D such that L is greater than D and preferably very much greater than D, D being the diameter of the circle in which the cross section of the fibre is inscribed. In particular, the ratio L/D (or aspect ratio) is chosen in the range from 3.5 to 2,500, preferably from 5 to 500 and better still from 5 to 150.

The fibres that may be used in the composition of the invention may be mineral or organic fibres, of synthetic or natural origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury.

In particular, the fibres have a length ranging from 1 µm to 10 mm, preferably from 0.1 mm to 5 mm and better still from 0.3 mm to 3 mm. They may have a cross section included within a circle with a diameter ranging from 2 nm to 500 µm, preferably ranging from 100 nm to 100 µm and better still from 1 µm to 50 µm. The weight or yarn count of fibres is often given in denier or decitex and represents the weight in grams per 9 km of yarn. Preferably, the fibres according to the invention have a yarn count chosen in the range from 0.01 to 10 denier, preferably from 0.1 to 2 denier and better still from 0.3 to 0.7 denier.

The fibres that may be used in the compositions according to the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in a content ranging from 0.5% to 30% by weight, more particularly from 2% to 25% by weight, relative to the weight of the composition. In accordance with a preferred embodiment of the invention, the content of fibres, if they are present, is less than or equal to 10% by weight and preferably less than or equal to 5% by weight, relative to the weight of the composition.

Additional Fillers

The term "fillers" should be understood as meaning colourless or white solid particles of any form, which are in a form that is insoluble and dispersed in the medium of the composition, and are of mineral or organic nature.

In the present patent application, "mineral filler" is understood to mean any mineral solid that is insoluble in the medium at room temperature (25° C.).

The term "mineral" refers to any compound or polymer whose chemical structure does not comprise any carbon atoms.

The fillers may or may not be surface-coated, and in particular they may be surface-treated with silicones, amino acids, fluoro derivatives or any other substance that promotes the dispersion and compatibility of the filler in the composition.

Such fillers are distinct from the mineral thickeners and also from the colouring agents described previously.

The fillers may be spherical, i.e. they may comprise at least a rounded general portion, preferably defining at least a sphere portion, preferably internally defining a concavity or a hollow (sphere, globules, bowls, horseshoe, and the like), or lamellar.

Such fillers are advantageously chosen from:
silica powders, such as the porous silica microspheres sold under the name Silica Beads SB-700 by the company Miyoshi or Sunsphere® H51 or Sunsphere® H33 by the company Asahi Glass; or the polydimethylsiloxane-coated amorphous silica microspheres sold under the name SA Sunsphere® H33 or SA Sunsphere® H-53 by the company Asahi Glass, acrylic (co)polymers powders and derivatives thereof, in particular
the polymethyl methacrylate powder sold under the names Covabead® LH85 by the company Wackherr or Microsphere M-100) by the company Matsumoto,
the polymethyl methacrylate/ethylene glycol dimethacrylate powder sold under the name Dow Corning 5640 Microsponge® Skin Oil Adsorber by the company Dow Corning or Ganzpearl® GMP-0820 by the company Ganz Chemical,
the polyallyl methacrylate/ethylene glycol dimethacrylate powder sold under the name Poly-Pore® L200 or Poly-Pore® E200 by the company Amcol Health and Beauty Solutions Inc.,
the ethylene glycol dimethacrylate/lauryl methacrylate copolymer powder sold under the name Polytrap® 6603 by the company Dow Corning,
optionally crosslinked acrylate/alkyl acrylate copolymer powder crosslinked acrylate/ethylhexyl acrylate copolymer powder sold under the name Techpolymer ACP-8C by the company Sekisui Plastics,
ethylene/acrylate copolymer powder, such as the product sold under the name Flobeads® by the company Sumitomo Seika Chemicals,
the expanded hollow particles of acrylonitrile (co) polymer sold under the name Expancel by Expancel or the microspheres sold under the name Micropearl F 80 ED® by the company Matsumoto,
the polyurethane powders sold, for example, under the names Plastic Powder D-400, Plastic Powder CS-400, Plastic Powder D-800 and Plastic Powder T-75 by the company Toshiki, silicone powders advantageously chosen from:
polymethylsilsesquioxane powders, in particular those sold under the name Tospearl, in particular Tospearl 145 A, by the company Momentive Performance Materials,
organopolysiloxane elastomer powders coated with silicone resin, especially with silsesquioxane resin, such as the products sold under the name KSP-100, KSP-101, KSP-102, KSP-103, KSP-104 or KSP-105 by the company Shin-Etsu (INCI name: vinyl dimethicone/methicone silsesquioxane crosspolymer),
silicone elastomer powders, such as the products sold under the name Trefil® Powder E-505C or Trefil® Powder E-506C by the company Dow Corning,
powders of organosilicone particles, for example, in the form of bowls, such as those described in JP-2003 128 788 or JP-A-2000-191789 or also in patent application EP 1 579 841 and sold especially by the company Takemoto Oil & Fat, polyamide powders, such as Nylon® powders, in particular Nylon 12 powders, such as the nylon powders sold under the name Orgasol® 2002 EXS NAT COS by the company Arkema, powders of natural organic materials, such as polysaccharide powders and in particular starch powders, especially crosslinked or non-crosslinked corn, wheat or rice starch powders, powders of starch crosslinked with octenylsuccinic anhydride sold under the name Dry-Flo® by the company National Starch or powders of waxy corn starch, such as those which are sold under the names C* Gel 04201 by the company Cargill, Corn Starch B by the company Roquette and Organic Corn Starch by the company Draco Natural Products, spherical cellulose microparticles, such as Cellulobeads D-10, Cellulobeads D-5 and Cellulobeads USF, sold by the company Daito Kasei Kogyo, particles of N—($C_8$-$C_{22}$ carbon atoms acylated) amino acids; the amino acid may be, for example, lysine, glutamic acid or alanine, preferably lysine, for example Amihope LL by the company Ajinomoto or the product sold under the name Corum 5105 S by the company Corum, Perlite powders, such as those sold by the company World Minerals under the trade name Perlite P1430, Perlite P2550, Perlite P2040 or OpTiMat™ 1430 OR or 2550 OR. Europerl EMP-2 and Europerl 1 by the company Imerys, zeolites, such as the products sold by the company Zeochem under the names Zeoflair 300, Zeoflair 200, Zeoflair 100, X-Mol and X-Mol MT, calcium magnesium carbonate particles, such as those sold by the company Imerys under the name Calcidol, by the company LCW (Sensient) under the name Carbomat or by the company Omya under the name Omyacare 60-AV.

Use may also be made of talc particles, for example sold under the names Luzenac Pharma M and UM by the company Imerys and Rose Talc and Talc SG-2000 by the company Nippon Talc; natural or synthetic mica particles, such as those sold under the names Mica M RP and Silk Mica by the company Merck, or the product sold under the name Sericite S-152-BC by the company Miyoshi Kasei; calcium carbonate and magnesium hydrogen carbonate; hydroxyapatite; boron nitride; fluorphlogopite; and mixtures thereof.

The spherical fillers may be coated with a hydrophobic treatment agent. The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof. The N-acylamino acids may comprise an acyl group containing from 8 to 22 carbon atoms, for instance a 2-ethyihexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine. The term "alkyl" mentioned in the compounds cited above especially denotes an alkyl group containing from 1 to 30 carbon atoms and preferably containing from 5 to 16 carbon atoms.

The composition advantageously has a content of additional filler(s) of between 0.5% and 30% by weight, more particularly from 2% to 15% by weight and preferably from 2% to 15% by weight, relative to the weight of the composition.

According to certain embodiments, the content of additional filler(s) is less than or equal to 10% by weight and preferably less than or equal to 5% by weight, relative to the weight of the composition. Preferably, the composition is free of fillers.

Hydrocarbon-Based Resin

The composition according to the invention also comprises at least one hydrocarbon-based resin chosen from indene hydrocarbon-based resins, pentanediene aliphatic resins, mixed resins of pentanediene and of indene, diene resins of cyclopentanediene dimers, diene resins of isoprene dimers, and mixtures thereof.

Preferably, the hydrocarbon-based resin has a number-average molecular weight of less than or equal to 10 000 g/mol, especially ranging from 250 to 5000 g/mol, better still less than or equal to 2000 g/mol, especially ranging from 250 to 2000 g/mol.

The number-average molecular weights (Mn) are determined by gel permeation liquid chromatography (THF solvent, calibration curve established with linear polystyrene standards, refractometric detector).

The resin of the composition according to the invention is advantageously a tackifying resin. Such resins are described especially in the Handbook of Pressure Sensitive Adhesive Technology, edited by Donatas Satas, 3rd edition, 1989, pages 609-619.

Preferably, the hydrocarbon-based resin is chosen from low molecular weight polymers that may be classified, according to the type of monomer they comprise, as:

indene hydrocarbon-based resins, preferably such as resins derived from the polymerization in major proportion of indene monomer and in minor proportion of a monomer chosen from styrene, methylindene and methyistyrene, and mixtures thereof. These resins may optionally be hydrogenated. These resins may have a molecular weight ranging from 290 to 1150 g/mol.

Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wngtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wngtack 86, Wngtack Extra and Wngtack Plus by the company Goodyear;

diene resins of cyclopentanediene dimers such as those derived from the polymerization of first monomers chosen from indene and styrene, and of second monomers chosen from cyclopentanediene dimers such as dicyclopentadiene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, β-pinene and limonene, and mixtures thereof. These resins can have a molecular weight ranging from 300 to 2000 g/mol. Such resins are sold, for example, under the names Piccolyte A115 and S125 by the company Hercules or Zonarez 7100 or Zonatac 105 Lite by the company Arizona Chem.

Mention may also be made of certain modified resins such as hydrogenated resins, for instance those sold under the name Eastotac C6-C20 Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

Preferably, the composition comprises at least one compound chosen from hydrocarbon-based resins as described previously, especially indene hydrocarbon-based resins and aliphatic pentadiene resins, or mixtures thereof. According to one preferred embodiment, the hydrocarbon-based resin is chosen from indene hydrocarbon-based resins.

According to one preferred embodiment, the resin is chosen from indene/methylstyrene/hydrogenated styrene copolymers.

In particular, use may be made of indene/methylstyrene/hydrogenated styrene copolymers, such as those sold under the name Regalite by the company Eastman Chemical, such as Regalite R 1100, Regalite R 1090, Regalite R-7100, Regalite R 1010 Hydrocarbon Resin and Regalite R 1125 Hydrocarbon Resin.

If the composition comprises at least one hydrocarbon-based resin, the content of this resin is less than or equal to 25% by weight, preferably ranging from 5% to 20% by weight, relative to the weight of the composition.

Optional Additives

The composition may comprise at least one optional ingredient chosen, for example, from film-forming agents other than the polymer particles described previously; antioxidants; preserving agents; fragrances; flavourings; neutralizers; emollients; organic thickeners; coalescers; moisturizers; vitamins, and mixtures thereof.

According to one embodiment of the invention, the composition comprises at least one plasticizer. In the case where the polymer particles are provided in the form of a dispersion, the plasticizer is then advantageously present in said oily dispersion.

The plasticizers may preferably be chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in a content ranging from 5% to 50% by weight relative to the total weight of the polymer particles.

Needless to say, a person skilled in the art will take care to select the optional additional additives and/or the amount thereof such that the advantageous properties of the composition according to the invention are not, or are not substantially, adversely affected by the envisaged addition.

The compositions according to the invention are thus intended for caring for and/or making up keratin materials, in particular the lips, and also keratin fibres especially such as the eyelashes or the eyebrows.

They advantageously contain a physiologically acceptable medium, in other words a medium that is compatible with the treated keratin materials.

The compositions according to the invention may be in fluid or solid form. Preferably, the compositions are in fluid form.

The term "fluid" refers to compositions for which it is possible to measure the viscosity at 25° C. and atmospheric pressure ($1.013 \times 10^5$ Pa).

The compositions according to the invention may also be in anhydrous form, or in the form of oil-in-water or water-in-oil emulsions.

If the compositions comprise water, the water content advantageously does not exceed 15% by weight and even more particularly does not exceed 10% by weight relative to the weight of the composition. Preferably, if it is present, the water content does not exceed 5% by weight relative to the weight of the composition.

In accordance with a preferred embodiment of the invention, the compositions are anhydrous.

The term "anhydrous" means that water is not deliberately added to the compositions, but may be present in trace amount in the various compounds used in the compositions.

Advantageously, the composition according to the invention is a makeup composition, in particular a mascara or a lipstick, preferably in fluid form.

Preferably, the hydrocarbon-based oil of the composition is chosen from volatile oils.

Needless to say, these compositions are advantageously pigmented. Reference may be made to the description as regards the nature and content of these compounds.

As regards mascaras, these compositions conventionally have a viscosity at 25° C. and atmospheric pressure ($1.013 \times 10^5$ Pa) of from 0.1 to 50 Pa·s, in particular from 1 to 30 Pa·s. In the case of mascaras, the viscosity is more particularly greater than or equal to 4 Pa·s (measured with a Rheomat RM100®).

According to one variant, in addition to the polymer particles that are preferably incorporated in the form of a dispersion in a hydrocarbon-based, preferably volatile, oil and the hydrocarbon-based block copolymer, the compositions comprise at least one hydrocarbon-based resin. The resin is preferably introduced in a content of between 5% and 20% by weight relative to the weight of the composition.

Advantageously, according to this variant, the content of non-volatile oil is less than 5% by weight relative to the weight of the composition. In accordance with an even more preferred embodiment, the composition is free of non-volatile oil.

According to another particular embodiment of this variant, the composition comprises a content of additional filler of less than 5% by weight, more particularly less than 2% by weight and even more preferentially less than 1% by weight, relative to the weight of the composition.

These variants may be combined.

As regards lip makeup compositions, they may be in a solid form (wand, dish) or in a fluid form (gloss) and preferably in fluid form. Usually, the viscosity of fluid lipstick compositions ranges from 0.3 Pa·s to 3 Pa·s (measured at 25° C. and $1.013 \times 10^5$ Pa).

According to one variant of the invention, in addition to the stabilized polymer particles and the block copolymer, the composition comprises at least one wax.

It should be noted that the content of wax is adjusted as a function of the desired galenical form (solid or fluid).

Preferably, said compositions comprise at least one plasticizer as described previously.

The invention is illustrated in more detail in the following examples.

All the percentages of reagents described in the examples are weight percentages.

EXAMPLES

Synthesis Examples

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 litres of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 litres of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 litre of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 litre of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Examples 7 and 8 (Invention) and 9 and 10
(Outside the Invention)

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 7

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a polyisobornyl acrylate stabilizer was obtained.

Example 8

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight A dispersion in isododecane of polymethyl acrylate particles stabilized with an isobornyl acrylate/methyl acrylate (85/15) statistical copolymer stabilizer was obtained.

Example 9 (Outside the Invention)

Step 1: 48.5 g of isobornyl acrylate, 12 g of methyl acrylate, 0.6 g Trigonox 21, 115 g of isododecane; followed by addition, after reaction, of 60 g of isododecane.

Step 2: 182 g of methyl acrylate, 1.82 g of Trigonox 21S, 182 g of isododecane. After reaction, addition of 60 g of isododecane and evaporation to obtain a solids content of 31% by weight A dispersion in isododecane of polymethyl acrylate particles stabilized with an isobornyl acrylate/methyl acrylate (80/20) statistical copolymer stabilizer was obtained.

Example 10 (Outside the Invention)

Step 1: 48.5 g of isobornyl acrylate, 21 g of methyl acrylate, 0.7 g Trigonox 21, 130 g of isododecane; followed by addition, after reaction, of 65 g of isododecane.

Step 2: 173 g of methyl acrylate, 1.73 g of Trigonox 21S, 173 g of isododecane. After reaction, addition of 65 g of isododecane and evaporation to obtain a solids content of 31% by weight A dispersion in isododecane of polymethyl acrylate particles stabilized with an isobornyl acrylate/methyl acrylate (70/30) statistical copolymer stabilizer was obtained.

The stability 12 hours after the end of synthesis of the oily dispersions of polymethyl acrylate of Examples 1 and 7 to 10 was compared, and the following results were obtained.

| Example | Stabilizer | Stability |
|---|---|---|
| 1 | 92 isobornyl acrylate/8 methyl acrylate | Stable |
| 7 | 100 isobornyl acrylate | Stable |
| 8 | 85 isobornyl acrylate/15 methyl acrylate | Stable |
| 9 | 80 isobornyl acrylate/20 methyl acrylate | Phase separation and setting to a solid |
| 10 | 70 isobornyl acrylate/30 methyl acrylate | Phase separation and setting to a solid |

The results obtained show that the dispersions of polymethyl acrylate in isododecane are stable when the stabilizer is an isobornyl acrylate homopolymer or an isobornyl acrylate/methyl acrylate copolymer with an isobornyl acrylate/methyl acrylate weight ratio>80/20.

Moreover, the film obtained with the oily dispersions of Examples 1, 7 and 8 have the following properties:

| Gloss at 20° | Resistance to fatty substances | Tacky |
|---|---|---|
| 72 | Resistant to fatty substances | Non-tacky |
| 69 | Resistant to fatty substances | Non-tacky |
| 65 | Resistant to fatty substances | Non-tacky |

Examples 11 and 12 (Outside the Invention)

Tests were performed with other monomers bearing a cyclic group by replacing the isobornyl acrylate, performing step 1 of Example 1, i.e. preparing a cyclic monomer/methyl acrylate (92/8) statistical copolymer stabilizer. All the stabilizers prepared in isododecane led to a medium that set to a solid in the form of a viscous precipitate. This shows that such stabilizers are unsuitable for forming an oily dispersion since they are incompatible with isododecane, in contrast with the stabilizers prepared in Examples 1 to 8 described previously.

| Examples | Stabilizer | Compatibility in isododecane |
|---|---|---|
| 11 | Cyclohexyl acrylate/methyl acrylate (92/8) | Incompatible (viscous precipitate) |
| 12 | Cyclohexyl methacrylate/methyl acrylate (92/8) | Incompatible (viscous precipitate) |

Examples 13: Mascara

The following compositions, the ingredients of which are given in the table below, are prepared.

The amounts are indicated by weight of starting materials.

| Ingredients | invention | comparative |
|---|---|---|
| Copolymer (methyl acrylate)-co-(isobornyl acrylate) in isododecane according to Example 1 | 48 | 48 |
| Styrene/isoprene block copolymer (Kraton ® G1701 from Kraton Polymers) | 8 | — |
| Ethylenediamine/stearyl dimer dilinoleate copolymer (Oleocraft LP-10-PA-(MV) from Croda) | — | 8 |
| Styrene/methylstyrene/indene copolymer (Regalite ® R1100CG Hydrocarbon Resin from Eastman) | 16 | 16 |
| Iron oxides (Sunpuro C33-7001, Sun) | 7 | 7 |
| Isododecane | 28 | 28 |

Protocol for Preparing Said Compositions

The components are weighed in a heating pan and placed in a Rayneri blender.

Once the gel has formed and is homogeneous, the mixture is left to cool to room temperature (25° C.) with stirring in the Rayneri blender. Each of the mascara compositions thus obtained is transferred into a closed container to prevent it from drying out on contact with air.

Evaluation of the Gloss

The composition is evaluated on a contrast card (for example Byko-charts by the company Byk-Gardner) by depositing a film of 150 µm which has dried for 24 hours at room temperature (25° C.).

The gloss of the film was measured using a Byk Spectro-guide 45/0 gloss glossmeter at 60°.

Results

The composition has a gloss of 81, whereas the comparative composition has a gloss, measured under the same conditions, of only 25.

The composition according to the invention is thus significantly more glossy.

Examples 14: Lipstick

The following compositions, the ingredients of which are given in the table below, are prepared. The amounts are indicated as weight of starting materials unless otherwise indicated.

| Ingredients | invention | comparative |
|---|---|---|
| Copolymer (methyl acrylate)-co-(isobornyl acrylate) in isododecane according to Example 1 | 50 | 50 |
| Hydrogenated styrene/butadiene copolymer (Kraton ® G-1657 polymer from Kraton Polymers) | 7.75 | — |
| Pigment (Red 7) | 5 | 5 |
| Isododecane | 37.26 | 45.01 |

Protocol for Preparing Said Compositions

A premix of Kraton with isododecane is prepared (25% Kraton in the mixture) at 100° C.

Separately, the mixture of the (methyl acrylate)-co-(isobornyl acrylate) copolymer in isododecane is homogenized with the remaining isododecane and the pigment.

The mixture containing the Kraton is then added to the preceding mixture at room temperature, and homogenized.

Results

Oil Resistance Test:

The composition is applied to an artificial keratin material support (25 µm thickness of the wet film).

The sample is left to dry for one hour at 37° C. with a relative humidity of 38%.

After the drying step, a drop of olive oil is placed on the film of composition and left for 10 minutes.

The oil is then wiped five times using cotton wool.

The integrity of the film after wiping with the cotton wool is observed to evaluate the oil resistance of the composition, on a scale ranging from 1 to 3 (1: excellent resistance, 2: intermediate resistance, and 3: poor resistance).

Transfer Test

The composition is applied to an artificial keratin material support (25 µm thickness of the wet film).

The sample is left to dry for one hour at 37° C. with a relative humidity of 38%.

After the drying step, a piece of adhesive tape is applied to the film of composition and removed at an angle of 180°.

The integrity of the film is observed after removing the adhesive tape and the transfer resistance is evaluated on a scale ranging from 1 to 3 (1: no peeling, 2: partial peeling, and 3: total peeling).

Results:

| | Composition according to the invention | Comparative composition |
|---|---|---|
| Oil resistance test | 1 | 2 |
| Transfer test | 1 | 2 |

The results show that the composition according to the invention has a persistence of the composition and a resistance to oil that are improved relative to the comparative composition not comprising Kraton.

The invention claimed is:

1. A composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one amorphous hydrocarbon-based block copolymer obtained by polymerization of at least one monomer of unsaturated hydrocarbon type comprising 2 to 5 carbon atoms and containing one or two ethylenic unsaturations.

2. The composition according to claim 1, wherein the polymer of the particles is a methyl acrylate and/or ethyl acrylate polymer.

3. The composition according to claim 1, wherein the polymer of the particles comprises an ethylenically unsaturated acid monomer or the anhydride thereof.

4. The composition according to claim 1, wherein the polymer of the particles comprises from 80% to 100% by weight of $C_1$-$C_4$ alkyl (meth)acrylate and from 0 to 20% by weight of ethylenically unsaturated acid monomer, relative to the total weight of the polymer.

5. The composition according to claim 1, wherein the polymer of the particles is chosen from:
   methyl acrylate homopolymers,
   ethyl acrylate homopolymers,
   methyl acrylate/ethyl acrylate copolymers,
   methyl acrylate/ethyl acrylate/acrylic acid copolymers,
   methyl acrylate/ethyl acrylate/maleic anhydride copolymers,
   methyl acrylate/acrylic acid copolymers,
   ethyl acrylate/acrylic acid copolymers,
   methyl acrylate/maleic anhydride copolymers, and
   ethyl acrylate/maleic anhydride copolymers.

6. The composition according to claim 1, wherein the stabilizer is a statistical copolymer of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than or equal to 5.

7. The composition according to claim 1, wherein the stabilizer is chosen from:
   statistical copolymers of isobornyl acrylate/methyl acrylate,
   statistical copolymers of isobornyl acrylate/methyl acrylate/ethyl acrylate, and
   statistical copolymers of isobornyl methacrylate/methyl acrylate.

8. The composition according to claim 1, wherein the hydrocarbon-based oil is an apolar hydrocarbon-based oil.

9. The composition according to claim 1, wherein the hydrocarbon-based oil is present in an amount of from 20% to 75% by weight relative to the weight of the composition.

10. The composition according to claim 1, wherein the surface-stabilized polymer particles, expressed as active material, is present in an amount of from 5% to 55% by weight expressed as polymer particle solids, relative to the weight of the composition.

11. The composition according to claim 1, wherein the hydrocarbon-based block copolymer comprises at least one styrene block and at least one block comprising units chosen from butadiene, ethylene, propylene, butylene and isoprene, or a mixture thereof.

12. The composition according to claim 11, wherein the hydrocarbon-based block copolymer is chosen from optionally hydrogenated diblock copolymers, of styrene-ethylene/propylene, of styrene-ethylene/butadiene, of styrene-ethylene/butylene, styrene-isoprene copolymers and optionally hydrogenated triblock copolymers, of styrene-ethylene/butadiene-styrene, of styrene-butylene/ethylene-styrene, of styrene-isoprene-styrene, of styrene-butadiene-styrene, and mixtures thereof.

13. The composition according to claim 1, wherein the hydrocarbon-based block copolymer is present in an amount of from 2.5% to 15% by weight, relative to the total weight of the composition.

14. The composition according to claim 1, further comprising at least one hydrocarbon-based resin chosen from indene hydrocarbon-based resins, pentanediene aliphatic resins, mixed resins of pentanediene and of indene, diene resins of cyclopentanediene dimers, diene resins of isoprene dimers, and mixtures thereof.

15. The composition according to claim 14, wherein the at least one hydrocarbon-based resin is present in an amount of less than or equal to 25% by weight relative to the weight of the composition.

16. The composition according to claim 1, wherein the polymer particles surface-stabilized with a stabilizer are incorporated into the composition in the form of a dispersion in at least one hydrocarbon-based oil.

17. The composition according to claim 11, wherein the hydrocarbon-based block copolymer is chosen from optionally hydrogenated diblock copolymers of styrene-ethylene/propylene, of styrene-ethylene/butylene, optionally hydrogenated triblock copolymers of styrene-butylene/ethylene-styrene, and mixtures thereof.

18. A process for making up and/or caring for keratin materials, comprising applying the composition according to claim 1 to the keratin materials.

* * * * *